(12) United States Patent
Bessos et al.

(10) Patent No.: US 6,479,246 B1
(45) Date of Patent: *Nov. 12, 2002

(54) COMPETITIVE BINDING ASSAY IMMUNOASSAY FOR PLATELET ANTIGENS IN WHOLE BLOOD

(75) Inventors: Hagop Bessos, Edinburgh (GB); William Gerrard Murphy, Dublin (IE)

(73) Assignee: Common Services Agency (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,457

(22) PCT Filed: Mar. 15, 1996

(86) PCT No.: PCT/GB96/00602

§ 371 (c)(1), (2), (4) Date: Nov. 20, 1997

(87) PCT Pub. No.: WO96/29600

PCT Pub. Date: Sep. 26, 1996

(30) Foreign Application Priority Data

Mar. 17, 1995 (GB) .............................................. 9505447

(51) Int. Cl.[7] .............................................. G01N 33/567
(52) U.S. Cl. ........................ 435/7.21; 435/7.1; 435/7.2; 435/7.9; 435/7.93; 436/538; 436/541
(58) Field of Search ........................... 435/7.93, 4, 7.1, 435/7.2, 7.21, 7.9; 436/538, 541

(56) References Cited

U.S. PATENT DOCUMENTS 4,607,009 A * 8/1986 Steplewski et al. ............. 435/7
5,478,741 A * 12/1995 Maret et al. ............ 435/240.27

FOREIGN PATENT DOCUMENTS

| EP | 0 028 133 | * | 5/1981 | .......... G01N/33/54 |
| WO | 94/11740 | * | 5/1994 | .......... G01N/33/80 |

OTHER PUBLICATIONS

Langenscheidt, et al.: Quantitation of platelet antigens after chloroquine treatment: Eur. J. Haem: 42: pp. 186–192, 1989.*

* cited by examiner

Primary Examiner—Jeffrey Stucker
(74) Attorney, Agent, or Firm—Myers Bigel Sibley & Sajovec

(57) ABSTRACT

A competitive binding assay kit and process for the immunological detection of a blood antigen of specified phenotype (for example phenotypes of human platelet antigen HPA) in a sample of whole blood. The kit contains a substrate having purified blood antigen of specified phenotype immobilized thereon, antibody specific to said blood antigen and means for enabling detection of antibody bound to said blood antigen. The process comprises mixing a sample of whole blood with a predetermined amount of antibody, so as to bind the antibody to any antigen present in the sample of whole blood and bringing the mixture into contact with the immobilized antigen so as to bind any remaining unbound antibody to the immobilized antigen, and determining the amount of immobilized complex and consequently the specified blood antigen phenotype.

17 Claims, 3 Drawing Sheets

Second Test

Third Test

COMPETITIVE BINDING ASSAY IMMUNOASSAY FOR PLATELET ANTIGENS IN WHOLE BLOOD

FIELD OF THE INVENTION

The present invention relates to a competitive binding assay kit and process for the immunological detection of a presence of a blood antigen of specified phenotype (for example phenotypes of HPA) in a sample of whole blood.

BACKGROUND OF THE INVENTION

Human Platelet Antigen 1 (HPA1), also known as PLA1, is a polymorphic determinant on the glycoprotein (GP) IIb/IIIa complex, that resides at the N-terminal region of GPIIIa. The great majority of the Caucasian population is homozygous or heterozygous for HPA1a (about 72% and 26% respectively) (1). However, 2–3% of the population is homozygous for HPA1b (PLA1 negative) putting them at risk from developing antibodies to HPA1a either during pregnancy or following transfusion with blood containing HPA1a platelets. For example, HPA1b pregnant women carrying HPA1a positive babies may produce anti-HPA1a antibodies which could lead to fetal or neonatal alloimmune thrombocytopenia (FAITP or NAITP) respectively, with 50% of the cases occurring at first pregnancy. One outcome of FAITP/NAITP, which has a frequency of 1 in 1000–2000 births, is intracranial hemorrhage with 6.5–10% mortality and 20% morbidity (neurological sequelae) (2).

Moreover, HPA1b individuals (mostly elderly multiparous women) transfused with blood containing HPA1a platelets may develop post-transfusion purpura (PTP) which is characterized with severe thrombocytopenia, 5–10 days following the transfusion. Although not as common as NAITP (only about 200 cases reported world-wide), PTP is nevertheless associated with 10–20% morbidity/mortality (3).

The treatment and management of FAITP/NAITP and PTP relies basically on several infusions of intra-venous IgG with or without transfusion with HPA1b platelets. In view of the serious or fatal outcomes of FAITP/NAITP and PTP and their increasingly effective treatment, antenatal screening for HPA1b is becoming widely accepted as an important prophylactic measure (4,5). For such wide-scale screening, established assays such as monoclonal antibody immobilization of platelet antigens (MAIPA), platelet suspension immunofluorescence test, or flow cytometry are not suitable due to their technical or financial burdens (6–8). Recently, Metcalfe et al reported a simplified method for large-scale HPA1a phenotyping for antenatal screening which was adapted from MAIPA (9). However, the Metcalfe et al assay relies on the extraction of glycoprotein GPIIb/IIIa antibody complex from platelets pre-incubated with the antibody. The assay is also considerably time consuming requiring a number of incubation and centrifugation steps.

EP 0028133 describes a method of detecting and quantitating haptens and antigens. A competitive binding assay is described in which a sample and a reagent containing an immunoreactive antibody are in a liquid phase, the sample and reagent either being mixed together or reacted before contacting a solid phase onto which a known concentration of a substance selected from haptens, antigens and/or mixtures thereof, which are also reactive with said antibody, is bound.

There is thus a requirement for an immunoassay which does not require a sample of whole blood to be substantially purified.

It is an object of the present invention to obviate and/or mitigate some of the above disadvantages.

Generally speaking the present invention provides a simple and potentially automatable competitive binding assay and assay kit for determining the presence in vitro of a specified blood antigen (for instance HPA1a) in a sample of whole blood. It is generally based on the surprising feature that the assay is able to determine a presence or absence of a specified blood antigen in a sample of whole blood. It might have been expected that cells and other species normally present in whole blood would interfere with such an assay.

SUMMARY OF THE INVENTION

The present invention provides in a first aspect a method of performing a competitive binding immunoassay for determining in vitro the presence of a specified blood antigen phenotype in a sample of whole blood, which comprises:

mixing the sample of whole blood with a predetermined amount of antibody specific to said blood antigen phenotype, so as to bind the antibody to any of said antigen present in the sample of whole blood;

bringing the mixture into contact with a substrate upon which antigen of said phenotype has been immobilized such as to bind any remaining unbound antibody to said immobilized antigen, thereby forming an immobilized antigen-antibody complex;

washing the immobilized antigen-antibody complex and;

estimating the amount of immobilized complex and consequently the specified blood antigen phenotype.

The present invention in a further aspect provides a competitive binding immunoassay kit for determining the presence of a specified blood antigen phenotype in a sample of whole blood which, comprises;

a substrate having immobilized thereon substantially pure blood antigen of said phenotype.

a supply of antibody for specifically binding to said antigen, and means for enabling detection of said specifically bound antibody.

The immunoassay of the present invention is described as a competitive binding immunoassay essentially because any blood antigen of said specified phenotype present in the whole blood sample competes with said immobilized antigen, for the predetermined amount of antibody.

The immunoassay can be used to detect the presence of any suitable intrinsic blood cell antigen of a specified phenotype (excluding foreign species such as viral antigens etc.). The blood antigens include antigenic determinants on platelet glycoproteins, in particular HPA1 antigen of 1*a* or 1*b* phenotype. Other antigens which are also suitable are glycoproteins or other determinants on blood cells, particularly white blood cells (such as granulocytes).

The sample of whole blood may be obtained fresh from an individual to be tested, or the blood may be from whole blood stored up to 25 days at 4° C. (for example citrated or EDTA whole blood). The whole blood sample may be used untreated, or alternatively the whole blood sample can be subjected to a washing step prior to testing (e.g. by diluting the blood, centrifuging it and resuspending in a buffer).

Typically, a sample of serum containing a high titer of antibody specific to said blood antigen may be employed in the immunoassay. Alternatively a monoclonal antibody specific to said blood antigen could be used.

The substrate upon which said substantially pure antigen of said phenotype is immobilized, can be any suitable substrate known in the art. Typically this can be paper, plastics such as nitrocellulose, or glass (e.g. microscope slides). Most preferably the substrate is a well of a plastics microtiter plate, as commonly employed in immunoassays.

The antigen to be immobilized is preferably substantially pure. That is, the antigen is purified away from other blood antigens or blood components that could affect the immunoassay. It is important that the antigen be substantially pure if the antibody used is in a serum sample. This is to prevent any additional antibodies that may be present in the serum sample, from binding to their respective blood antigen. If a monoclonal antibody is employed, it may not be necessary to highly purify the antigen, depending on the degree of cross-reactivity of the monoclonal antibody which should be specific to its specified antigen. The antigen used should be purified from a blood source, different to that being tested. This is to minimize any further antigen-antibody complexes which may be formed, from interfering with the immunoassay.

Typically a number of immune (i.e. antigen-antibody) complexes may be formed when bringing the mixture into contact with the substrate, for instance; a) specified antibody and immobilized antigen, b) specified antibody and antigen present in the whole blood, and c) non-specifically bound unspecified antibody to immobilized antigen. The washing serves to remove all complexes except the specified antibody and immobilized antigen complex.

The mixing of the sample of whole blood with antibody and the bringing the mixture into contact with the substrate can be carried out concurrently, or alternatively as two separate steps.

Generally, the substrate bound immune complex is estimated by means of anti-human IgG or IgM labelled with an appropriate label, such as an enzyme label (e.g. horseradish peroxidase HRP), a radiolabel, a fluorescence label or other labelling system known in the art. Using an enzyme label, an enzyme-linked immunosorbent assay (ELISA) may be provided which is sensitive, specific, cheap, quick and could potentially be used for large scale automated screening for whole blood antigens. Advantageously, it has been found that the incubations involved in the production of the immune complex, and the estimation thereof with labelled antibody can be carried out at room temperature and so do not require the use of an incubator.

It is envisaged that a particularly preferred immunoassay would involve detection of HPA1a antigen. The antigenic determinant for HPA1a is present on the GPIIIa subunit, so that a competitive binding immunoassay to detect the presence HPA1a antigen in a whole blood sample, would include immobilized HPA1a antigen. Typically this can be HPA1a typed platelets (which have been previously genotyped, for instance by using the technique described in Williamson, et al (13)), purified glycoprotein complex GPIIb/IIIa (prepared, for example, by the process described in Bessos et al (10)), purified glycoprotein GPIIIa, or synthetically manufactured HPA1a antigen.

In a particularly preferred embodiment of the first aspect, the present invention provides a method of performing a competitive binding immunoassay for determining in vitro the presence of HPA1a antigen in a sample of whole blood, which comprises;

mixing the sample of whole blood with a predetermined amount of anti-HPA1a antibody, so as to bind the antibody to any HPA1a antigen present in the sample of whole blood;

bringing the mixture into contact with a substrate upon which HPA1a antigen has been immobilized, such as to bind remaining anti-HPA1a antibody to the immobilized HPA1a antigen, thereby forming an immobilized HPA1a antigen—anti-HPA1a antibody complex;

washing the immobilized HPA1a antigen—anti-HPA1a antibody complex; and estimating the amount of immobilized complex and consequently HPA1a antigen.

In a particularly preferred embodiment of the further aspect, the present invention provides a competitive binding immunoassay kit for determining the presence of HPA1a antigen in a sample of whole blood which comprises;

a multiwell microtiter plate or plates having a well containing immobilized substantially pure HPA1a antigen;

a supply of anti-HPA1a antibody for specifically binding to said HPA1a antigen, and means for enabling detection of said specifically bound antibody.

Typically, each well contains 0.05 $\mu$g to 0.5 $\mu$g of antigen per well; preferably 0.1 $\mu$g of antigen per well.

The substrate upon which HPA1a antigen has been immobilized is generally blocked with a non-specific protein mixture, such as bovine serum albumin prior to bringing the mixture into contact with the substrate.

BRIEF DESCRIPTION OF THE DRAWINGS

Embodiments of the present invention will now be described by way of example only, with reference to the Figures which show.

DETAILED DESCRIPTION OF PREFERRED EMBODIMENTS

EXAMPLE 1

Purification of GPIIb/IIIa

Figure 1:
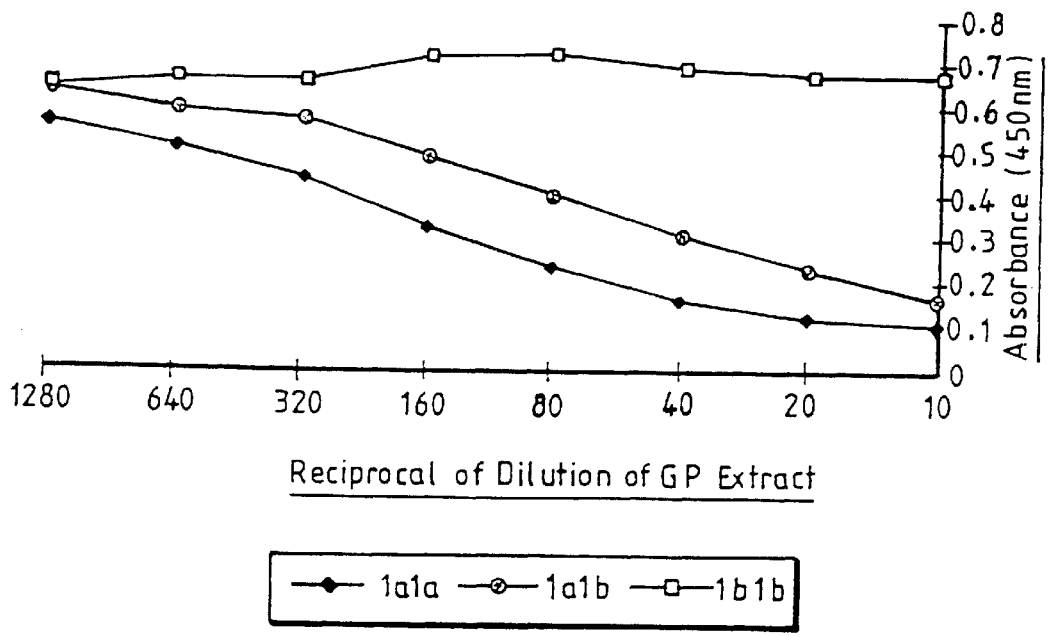
FIG. 1 shows the distinction between HPA1a positive and negative GP extracts, using anti-serum T.

The various reagents used were of the Analar grade and were purchased from ICN(UK), Sigma(UK), or Aldrich Chemicals Ltd, (UK). Anti-HPA1a sera were obtained from mothers of babies with NAITP. HRP-conjugated sheep anti-human IgG was provided by the Scottish Antibody Production Unit, and bovine serum albumin (BSA), Boseral, was purchased from Organon Technika (Holland). Synthetic peptides and CNBr activated Sepharose 4B were purchased from Calbiochem/Novabiochem (UK) and Pharmacia Ltd. (UK) respectively. Genotyped platelets (either separated and washed or in whole blood) were used to assess the performance of the new CB assay.

Platelet membrane glycoprotein GPIIb/IIIa was extracted and purified essentially as described before (10, 11). Briefly, a unit of HPA1a1a, HPA1a1b, or HPA1b1b apheresed platelet concentrate (PC) was washed and extracted with 100 mM octylglucopyranoside and 2 mM phenylmethylsulfonyl fluoride in buffer containing 50 mM Tris/HCl and 150 mM NaCl, pH 7.5 (TBS). The extract was supplemented with cations and mixed end-over-end with 2 g of immobilized synthetic peptide GRGDSPK (at 12 mg peptide/g Sepharose 4B) overnight at 4° C. The Sepharose beads were then centrifuged (1,000 for 5 min at room temperature), and the supernatant removed. The GPIIb/IIIa adsorbed beads were washed several times before eluting with cation enriched buffer (1 mM $MgCl_2$ and 1 mM $MnCl_2$) containing synthetic peptide GRGDSP. The eluate was dialyzed twice at 4° C. against a liter of Tris/HCl buffer (10 mM Tris/HCl, 150 mM NaCL pH 7.4) and stored frozen in aliquots at −40° C. until needed. Typically, about 1 mg of GPIIb/IIIa was removed from each unit of apheresed PC with 95% purity.

EXAMPLE 2

Determination of a Suitable Anti-HPA1a Serum and its Ability to Distinguish Between Soluble GPIIb/IIIa of Different HPA Phenotypes The binding of three anti-HPA1a sera to coated HPA1a1a was assessed in serial doubling dilutions, of which only two (C and T) exhibited satisfactory binding (data not shown) (10). Limiting antibody dilutions giving 50% maximum binding (1:40 for both antisera) were used to develop the CB assay. In the first instance, antibody binding in the presence of serial doubling dilutions of soluble HPA1a1a and HPA1b1b GP (starting at 4 ug/ml) was compared. Both antisera (C and T) were found to distinguish between the two phenotypes.

EXAMPLE 3

Competitive Binding (CB) Assay

The whole blood or platelet samples obtained from normal volunteers were washed or diluted in platelet wash buffer consisting of 148 mM NaCl, 5 mM glucose, 0.6 mM EDTA, and 20 mM Tris, pH 7.4. The washing of microtiter plate wells in the ELISA was carried out in ELISA wash buffer consisting of 137 mM NaCl, 1.5 mM $KH_2PO_4$, 8.1 mM $Na_2HPO_4 \cdot 12H_2$, 2.7 mM KCl, and 0.05% Tween$^{RTM}$ 20, pH 7.5.

The basic coating, blocking, washing, and color development procedures of the CB ELISA were as described previously (10,12). Maxisorp immuno-plates IF (A/S Nunc, Denmark) were coated with 100 $\mu$l/well of purified HPA1a1a GPIIb/IIIa at 1 $\mu$g/ml overnight at 4° C. and blocked with 5% BSA (in coating buffer) for 1 hr at room temperature (RT) [wells with coating buffer but without GPIIb/IIIa were included as controls for background binding].

Initially, for determining a suitable anti-HPA1a serum, the wells were washed with ELISA wash buffer and sera added in triplicate in serial doubling dilutions, at 100 $\mu$l/well and incubated for 1 hr. The results were plotted on a graph (data not shown) and this resulted in a sigmoid curve, from which the dilution of antibody giving 50% maximum binding could be determined. This "limiting" antibody amount would enable competition between cellular HPA1a antigen and the coated antigen for the antibody.

For development of the CB assay, purified GPIIb/IIIa, citrated or EDTA whole blood at 1:10 in platelet wash buffer (i.e. 1:20 once mixed with antibody—see below), or washed platelets in platelet wash buffer (all of various phenotypes), were added in triplicate to the wells at 50 $\mu$l/well. The wells were then supplemented with 50 $\mu$l/well of anti-HPA1a serum at 1:20 in ELISA wash buffer (i.e. 1:40 final dilution) and the plate gently shaken (rotatest Shaker, Luckham, UK) for 1 hr at RT. This allows competition between coated HPA1a GPIIb/IIIa and its corresponding phenotype on the soluble GP or platelets (either separated or in whole blood) for the predetermined amount of anti-HPA1a serum. The same HPA phenotype (HPA1a) present in a sample would significantly inhibit the binding of the antibody to the immobilized antigen in the wells, whereas HPA1b would not. After the incubation, the plates were washed by squirting ELISA wash buffer 3×100 $\mu$l/well up to ten times. Anti-HPA1a antibody bound to the wells was detected by incubation with HRP-conjugated sheep anti-human IgG at 1:400 in ELISA wash buffer (100 $\mu$l/well), before washing and developing the color as previously described (12). Specific binding was obtained by subtracting the absorbence in wells coated with buffer only from those coated with purified GPIIb/IIIa.

EXAMPLE 4

CB Assay Using GP Extracted from Platelets with Different HPA1 Phenotypes

Non-purified extracts obtained from phenotyped washed platelets (by Octyl glucopyranoside detergent extraction as mentioned above) were tested in the CB assay in serial doubling dilutions (starting at 1:10). As shown in FIG. 1 there was a clear distinction between HPA1a1a or HPA1a1b and HPA1b1b GP extracts indicating the suitability of the assay for determining platelet phenotypes using extracted GP.

EXAMPLE 5

CB Assay Using Washed Platelets from HPA1a and HPA1b Volunteers

Figure 2:
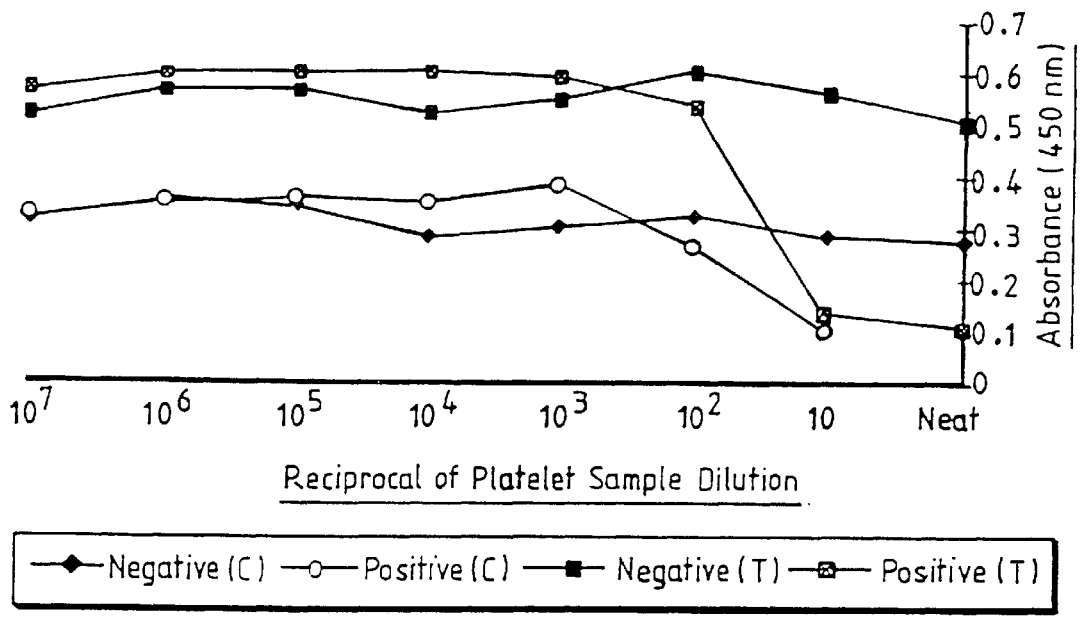
FIG. 2 shows the distinction between HPA1a positive and negative platelets, using anti-serum T and anti-serum C.

Citrated blood samples (10 ml) obtained from an HPA1a and an HPA1b volunteer were centrifuged at 750 g for 10 minutes, RT, and the buffy coat removed, washed twice with platelet wash buffer, resuspended in wash buffer to similar platelet count, and tested in serial dilutions of 10×. HPA1a platelets caused significant inhibition of antibody binding, while HPA1b platelet showed none (FIG. 2). Since antiserum T consistently showed a better distinction between the two phenotypes, it was chosen for routine use in the CB assay. Repeats of this experiment indicated that variation within normal platelet count was not critical to the observed distinction between the two phenotypes (data not shown).

EXAMPLE 6

Figure 3:
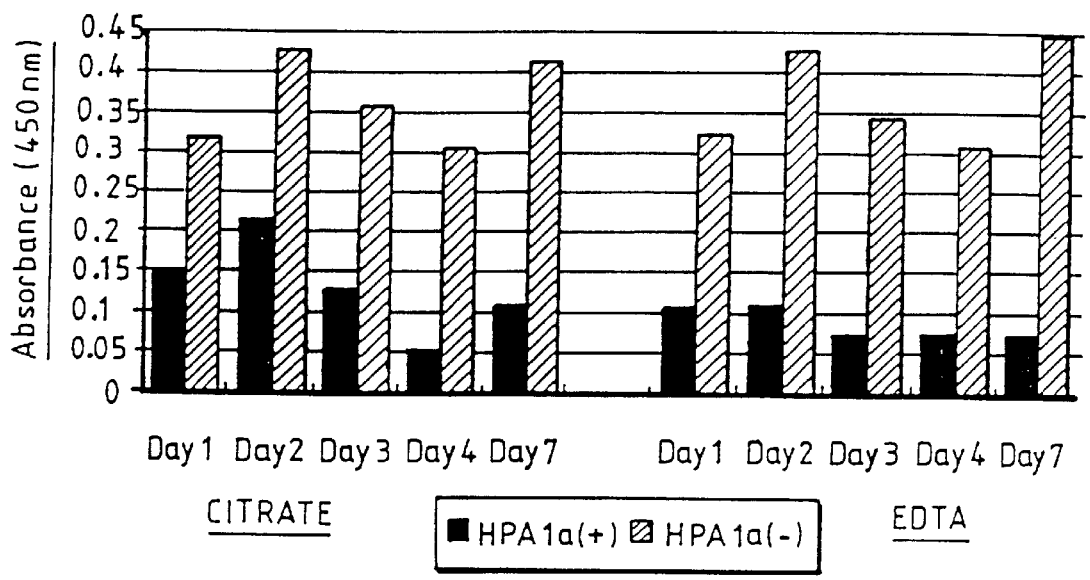
FIG. 3 shows the distinction between HPA1a positive and negative samples using fresh and stored whole blood.

CB Assay Using Fresh and Stored Citrated or EDTA Whole Blood Obtained from HPA1a and HPA1b Volunteers Once the applicability of the assay was tested with extracted GP and intact platelets, its applicability to non-manipulated whole blood was investigated. Both citrated and EDTA whole blood was obtained from an HPA1a and an HPA1b volunteer and stored at 4° C., and tested at 1:10 in platelet wash buffer at various intervals of time. As shown in FIG. 3, the specific absorbence using HPA1a blood was consistently distinct from HPA1b blood up to day 7 of storage. The procedure described in example 3 was followed, with the following exceptions: the wells were washed 7× after incubation with blood on days 1 and 2, and 10× for the rest of the storage period in order to improve the relatively inferior performance of the assay on citrated blood on the first two days.

EXAMPLE 7

Assessment of CB Assay Performance by Testing Genotyped Samples Blind

Figure 5:
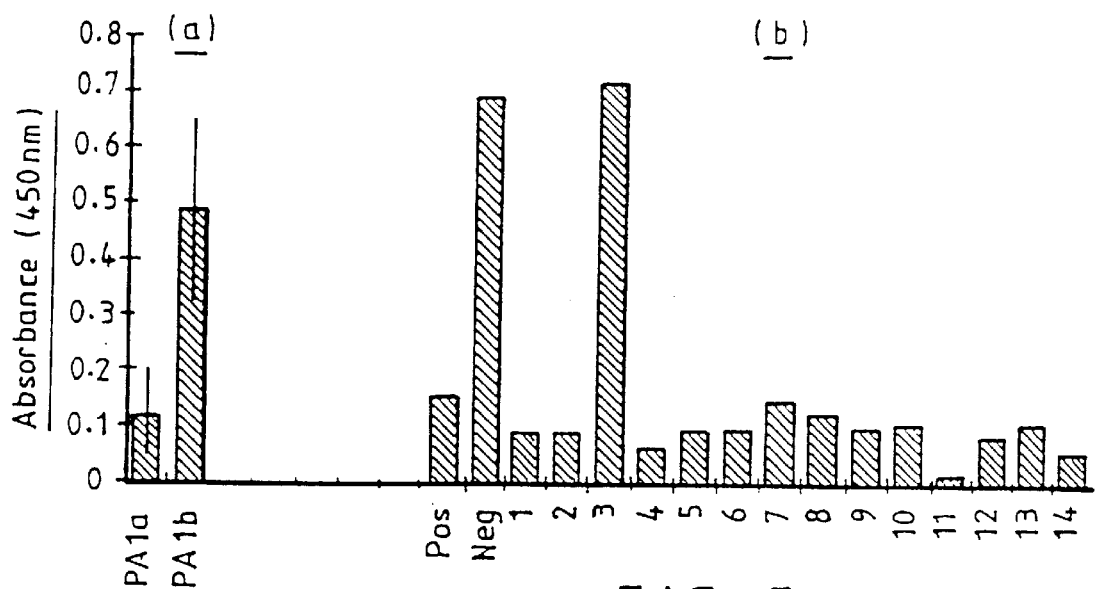
FIG. 5 shows a representative set of assay results obtained from a study of 475 blood samples.
Figure 4:
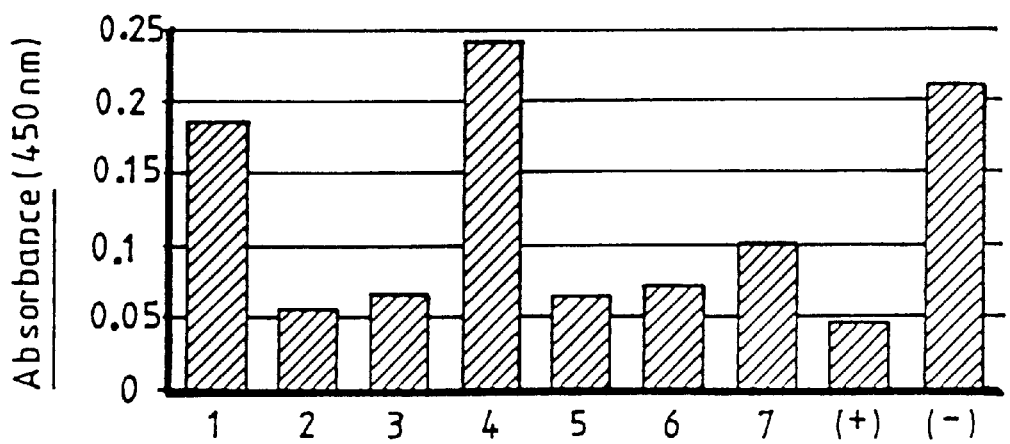
FIG. 4 shows an assessment of the competitive binding assay performance using 33 previously genotyped blood samples, compared to positive and negative controls.
Figure 4:
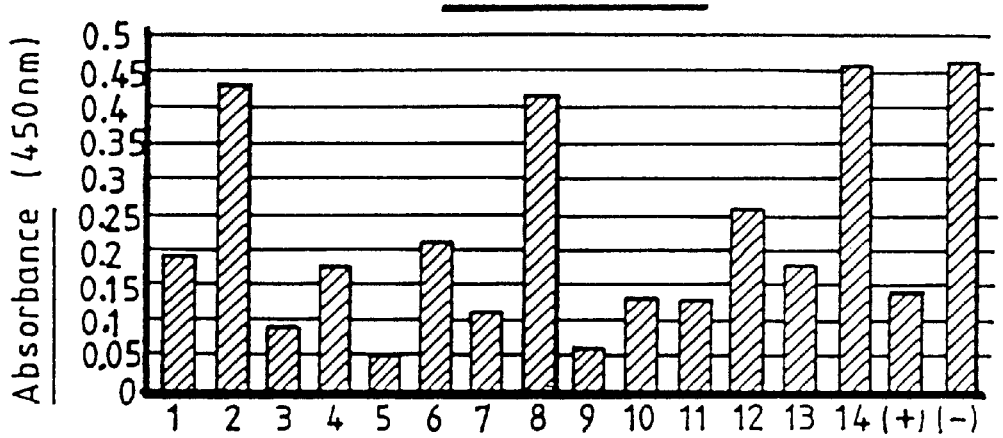
Figure 4:
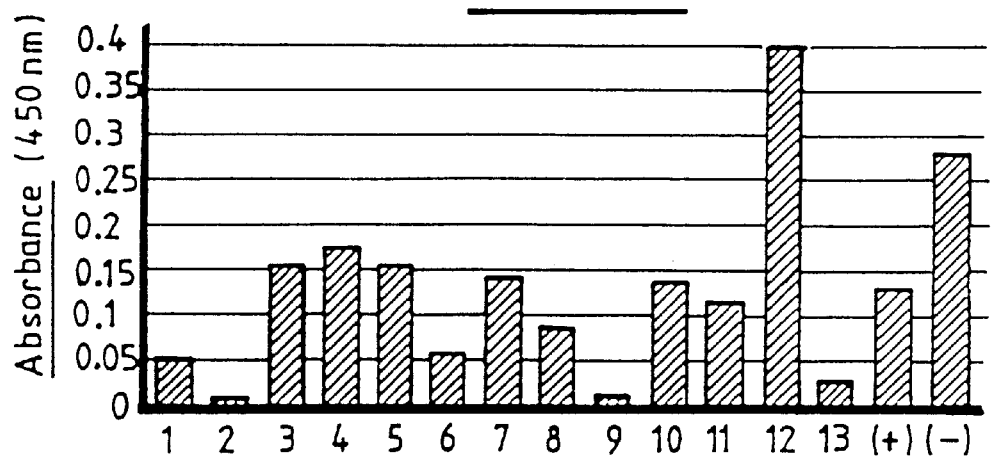

In order to assess the performance of the assay three sets of different tests were carried out at different times using blind samples obtained from the Cambridge Regional Blood Transfusion Centre. These samples consisted of EDTA blood genotyped as described in a recent review article by Williamson et al. (13). The assay procedure according to example 3 was followed to assay blood samples at 1:10 dilution using anti-serum T. In each test HPA1a positive and negative controls stored at 4° C. were included. In the first test the controls were 3 day old blood samples. In the second test the controls were 8 day old blood samples. In the third test the controls were 15 day old samples. The CB assay exhibited a very satisfactory performance (FIG. 4) correctly determining the phenotypes of all samples, including 6 HPA1b samples (nos. 1 and 4, first test; nos. 2, 8, 14, second test; and no. 12, third test). Following these experiments, the assay was altered to maximize the signal to noise ratio by the addition of an initial whole blood washing step: 5 ml blood at 1:10 diluted in platelet wash buffer is spun at 750 g for 10 minutes at room temperature, and the cells resuspended in 1 ml platelet wash buffer (see FIG. 5 for improvement in signal to noise ratio).

EXAMPLE 8

A Comparative Study of the CB Assay Against the Capture-P Kit Assay

The CB assay of the present invention was compared against the commercially available Capture-P kit assay (Immucor Inc., U.S.A.). The procedure according to example 3 was followed together with a preliminary washing step of whole blood using a 1:10 dilution in platelet wash buffer.

475 samples were tested and the CB assay and Capture-P kit assay were in 100% agreement (468 HPA1a positive and 7 HPA1a negative). The mean absorbances of HPA1a and HPA1b samples were 0.12 (SD 0.08) and 0.49 (SD 0.16) respectively, $P<0.0005$, Student's t test (FIG. 5a). An example of the histograms obtained using the CB assay is shown in FIG. 5b, where sample number 3 is clearly HPA1b. (Positive and negative imply HPA1a positive and HPA1a negative [i.e. HPA1b], controls respectively). Controls in these series of tests comprised HPA1a or HPA1b whole blood stored for up to 25 days at 4 C. (preliminary results also showed that soluble HPA 1a and 1b GP could serve as alternative controls—data not shown).

Although there was background binding in the CB assay (in wells not coated with antigen), it was possible to obtain a clear distinction between HPA1a positive and negative platelet phenotypes. Generally two factors appear critical for this distinction: firstly, the use of a strong anti-HPA1 antiserum; and secondly, excessive washing of wells at the end of incubation with whole blood. The excessive washing was required not only to remove non-specifically bound IgG but also any bound anti-GPIIb/IIIa antibodies which may be present occasionally in some samples (such as those obtained from immune thrombocytopenia patients). Such antibodies are probably not as strong as the anti-HPA1a antibody and thus may not pose a problem in the assay.

The present assay is ideally suited for large scale screening of antenatal samples for the following reasons; it only requires the use of non-manipulated blood; it incorporates only small amounts of anti-HPA1a serum (2.5 µl/well); and is easily automatable. Large scale screening should detect mothers at risk from FAITP or NAITP so that they could be followed closely during pregnancy to detect signs of fetal thrombocytopenia with or without the emergence of anti-HPA1a antibodies.

REFERENCES

1. Newman P: Platelet GPIIb/IIIa: molecular variations and alloantigens. Thromb. Haemost. 66: 111, 1991.
2. Mueller-Eckhardt C, Mueller-Eckhardt G, Willen-Ohff H, Horz A, Kuenzlen E, O'Neill G J, Schendel D J; Immunogenecity of and immune response to the human platelet antigen $ZW^a$ is strongly associated with HLA-B8 and DR3. Tissue Antigens 26:71, 1985.
3. Mueller-Eckhardt C: Post-transfusion Purpura. Br. J. Haematol. 64: 419, 1986.
4. Gafni A, Blanchette, V S: Screening for neonatal alloimmune thrombocytopenia: an economic perspective. In: Current Studies in Haematology and Blood Transfusion (eds. Decary F, Rock G), 140. Karger, Basel, 1988.
5. Waters A, Murphy M, Hambley H, Nicolaides K; Management of allommune thrombocytopenia in the fetus and neonate. In: Clinical and Basic Science Aspects of Immunohaematology (ed. Nance S J), 155. American Association of Blood Banks, Arlignton, Va., 1991.
6. Borne Kr Von Dem D E G, V E R Heught F W A, OosterhofF, Riesz Von E, Brutel de la Riviere A, Engelfriet C P: A simple immunofluorescence test for the detection of platelet antibodies. Br. J. Haematol. 39; 195, 1978.
7. Freedman J, Hornstein A: Simple method for differentiating between HLA and platelet specific antibodies by flow cytometry. Am. J. Haematol. 38: 314, 1991.
8. Kiefel V: The MAIPA assay and its application in immunohaematology. Transfusion Med. 2. 181, 1992.
9. Metcalfe P, Doughty H A, Murphy M F, Waters H: A simplified method for large-scale HPA-1a phenotyping for antenatal screening. Transfusion Med. 4: 21, 1994.
10. Bessos H, Goldschmeding R, Borne Von Dem A K R, Atkinson A, Murphy W G: The development of a simple and quick enzyme-linked immunosorbent assay for anti-HPA1a (PLA1) antibodies. Thromb. Res. 69: 395, 1993.
11. Kirchhofer D, Pierschbacher M D, Ginsberg M H, Plow E F<Ruoslahti E: Platelet membrane glycoprotein IIb/IIIa: a member of a family of Arg-Gly-Asp-specific adhesion receptors. Science 231: 1559, 1990.
12. Bessos H, Murphy W G: A new competitive binding enzyme-linked immunosorbent assay for glycocalicin in plasma and platelet concentrate supernatants. Thromb. Res. 59: 497, 1990.
13. Williamson L M, Bruce D, Lubenko A, Chana H J, Ouwehand W H: Molecular biology for platelet allantigen typing. Transfusion Med. 2: 255, 1992.

What is claimed is:

1. A method of performing a competitive binding immunoassay for determining in vitro the presence of a specified blood antigen phenotype in a sample of whole blood, where said blood antigen phenotype comprises platelet blood antigens, and wherein said method comprises:

(a) contacting a sample of whole blood with a predetermined amount of antibody specific to said blood antigen phenotype, so as to bind the antibody to any of said antigen present in the sample of whole blood;

(b) contacting the mixture of step (a) with a substrate upon which antigen of said phenotype has been immobilized such as to bind any remaining unbound antibody to said immobilized antigen, thereby forming an immobilized antigen-antibody complex;

(c) washing the immobilized antigen-antibody complex; and (d) detecting the amount of immobilized antigen-antibody complex, wherein the amount of immobilized antigen-antibody complex indicates the presence of said blood antigen phenotype.

2. A method of performing a competitive binding immunoassay according to claim 1 wherein the whole blood is washed by dilution, centrifugation and resuspension in a buffer prior to contacting the antibody.

3. A method of performing a competitive binding immunoassay according to claim 1 wherein step (a) comprises contacting said sample of whole blood with a sample of serum containing said predetermined amount of antibody specific to said blood antigen phenotype.

4. A method of performing a competitive binding immunoassay according to either of claims 1 or 2 wherein the antibody is a monoclonal antibody specific to said blood antigen.

5. A method of performing a competitive binding immunoassay according to claim 1 wherein the substrate is a well of a microtiter plate.

6. A method of performing a competitive binding immunoassay according to claim 1 wherein the antigen to be immobilized is purified and as such is purified away from other blood antigens or blood components.

7. A method of performing a competitive binding immunoassay according to claim 6 wherein the antigen to be immobilized is purified from a blood source different from the subject being tested.

8. A method of performing a competitive binding immunoassay according to claim 1 wherein steps (a) and (b) are carried out concurrently.

9. A method of performing a competitive binding immunoassay according to claim 1 wherein steps (a) and (b) are carried out as two separate steps.

10. A method of performing a competitive binding immunoassay according to claim 1 wherein the immobilized antigen-antibody complex is estimated by means of an anti-human antibody labelled with an appropriate label, selected from the group consisting of an enzyme label, a radiolabel, and a fluorescence label.

11. A method of performing a competitive binding immunoassay according to claim 1 wherein the method is carried out at room temperature.

12. A method of performing a competitive binding immunoassay according to claim 1 wherein the immunoassay detects the presence of HPA1a antigen in a whole blood sample and said immobilized antigen is HPA1a antigen.

13. A method of performing a competitive binding immunoassay according to claim 12 wherein the immobilized HPA1a antigen is selected from the group consisting of HPA1a typed platelets, , purified glycoprotein complex GPIIb/IIIa, purified glycoprotein GPIIIa, and synthetically manufactured HPA1a antigen.

14. A method of performing a competitive binding immunoassay for determining in vitro the presence of HPA1a antigen in a sample of whole blood, wherein said method comprises:

(a) contacting the sample of whole blood with a predetermined amount of anti-HPA1a antibody, so as to bind the antibody to any HPA1a antigen present in the sample of whole blood;

(b) contacting the mixture of step (a) with a substrate upon which HPA1a antigen has been immobilized, such as to bind remaining anti-HPA1a antibody to the immobilized HPA1a antigen, thereby forming an immobilized HPA1a anitgen-anti-HPA1a antibody complex;

(c) washing the immobilized HPA1a antigen-anti-HPA1a antibody complex; and (d) detecting the amount of immobilized complex, wherein the amount of immobilized antigen-antibody complex indicates the presence of HPA1a antigen in said sample of whole blood.

15. A competitive binding immunoassay kit for determining the presence of HPA1a antigen in a sample of whole blood which comprises;

at least one microwell microtiter plate having at least one well containing immobilized purified HPA1 a antigen;

anti-HPA1a antibody for specifically binding to said HPA1a antigen, and means for detecting said specifically bound antibody.

16. A competitive binding immunoassay kit according to claim 15 wherein said well containing immobilized HPA1a antigen contains 0.05 µg to 0.5 µg of antigen.

17. a competitive binding immunoassay kit according to claim 15 wherein the substrate upon which HPA1a antigen has been immobilized has been blocked with a non-specific protein mixture.

\* \* \* \* \*